United States Patent
Fukuoka

(10) Patent No.: US 10,345,225 B2
(45) Date of Patent: Jul. 9, 2019

(54) ANALYZER, ABSORPTION CHARACTERISTIC CALCULATION CIRCUIT, AND ANALYSIS METHOD

(71) Applicant: SUMITOMO ELECTRIC INDUSTRIES, LTD., Osaka (JP)

(72) Inventor: Takashi Fukuoka, Osaka (JP)

(73) Assignee: SUMITOMO ELECTRIC INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/014,177

(22) Filed: Jun. 21, 2018

(65) Prior Publication Data

US 2018/0372620 A1   Dec. 27, 2018

(30) Foreign Application Priority Data

Jun. 23, 2017  (JP) .................................. 2017-123448

(51) Int. Cl.

| | |
|---|---|
| *G01N 21/17* | (2006.01) |
| *G01J 3/42* | (2006.01) |
| *H01S 5/0625* | (2006.01) |
| *G01N 21/39* | (2006.01) |
| *G01J 3/10* | (2006.01) |
| *G01J 3/28* | (2006.01) |
| *H01S 5/062* | (2006.01) |
| *H01S 5/34* | (2006.01) |
| *G01N 21/3504* | (2014.01) |

(52) U.S. Cl.
CPC ............ *G01N 21/1702* (2013.01); *G01J 3/10* (2013.01); *G01J 3/28* (2013.01); *G01J 3/42* (2013.01); *G01N 21/39* (2013.01); *H01S 5/06213* (2013.01); *H01S 5/06255* (2013.01); *G01N 21/3504* (2013.01); *G01N 2021/399* (2013.01); *H01S 5/0622* (2013.01); *H01S 5/3401* (2013.01)

(58) Field of Classification Search
CPC ........... G01N 21/3504; G01N 21/3103; G01N 21/359; G01N 21/1702; G01N 2201/0612; G01J 3/42; H01S 5/3401; H01S 5/06255
(Continued)

(56) References Cited

U.S. PATENT DOCUMENTS

| | | | |
|---|---|---|---|
| 9,310,295 B2 * | 4/2016 | Tabaru ................... G01N 21/39 |
| 2010/0242572 A1 * | 9/2010 | Yu ....................... G01N 21/1702 73/24.02 |

(Continued)

OTHER PUBLICATIONS

T. K. Subramaniam, "Quantum Cascade Laser in Atmospheric Trace Gas Analysis", *AASCIT Journal of Environment*, vol. 1, No. 1, pp. 1-4, (Apr. 2015).

(Continued)

*Primary Examiner* — Hoa Q Pham
(74) *Attorney, Agent, or Firm* — Smith, Gambrell & Russell, LLP

(57) ABSTRACT

An analyzer includes a quantum cascade laser that converts a cyclic driving signal to laser light; an optical receiver that receives the laser light having passed through a sample and outputs a detected signal depending on intensity of the laser light; and a data calculation portion that outputs information representing absorption characteristics of the sample. The data calculation portion includes a delaying unit that produces a time-delayed waveform by applying a time delay to a reference driving signal; an adding unit that produces a symmetrical waveform by adding the time-delayed waveform and the detected signal; a time inversion unit that produces a time-inverted waveform by time-inverting the symmetrical waveform; and a subtracting unit that produces a waveform difference between the time-inverted waveform and the symmetrical waveform. The data calculation portion repeatedly calculates the waveform difference by changing the time delay until the waveform difference is minimized.

7 Claims, 11 Drawing Sheets

(58) Field of Classification Search
USPC ..... 356/432–440; 250/338.1, 339.12, 339.13
See application file for complete search history.

(56) References Cited

U.S. PATENT DOCUMENTS

| | | | | |
|---|---|---|---|---|
| 2012/0113426 A1* | 5/2012 | Rao | ................. | G01J 3/4338 |
| | | | | 356/437 |
| 2015/0226666 A1* | 8/2015 | Harb | ................. | G01N 21/031 |
| | | | | 356/432 |
| 2017/0373461 A1* | 12/2017 | Nogiwa | ............. | H01S 3/0941 |

OTHER PUBLICATIONS

Jonas Kottman et al., "Mid-Infrared Photoacoustic Detection of Glucose in Human Skin: Towards Non-Invasive Diagnostics", *Sensors* (Oct. 2016).

Jane Hodgkison and Ralph P. Tatam, "Optical gas sensing: a review", *Measurement Science and Technology*, 24 (2013).

Lionel Tombez, "Analysis and Improvement of the Spectral Properties in Mid-Infrared Semiconductor Quantum Cascade Lasers", *Doctoral Thesis, Université De Neuchâtel* (2014).

Andreas Hangauer et al., "High-speed Modulation Characteristic of a Quantum Cascade Laser", *Conference Paper, ResearchGate* (Jun. 2013).

* cited by examiner

ANALYZER, ABSORPTION CHARACTERISTIC CALCULATION CIRCUIT, AND ANALYSIS METHOD

BACKGROUND OF THE INVENTION

1. Field of the Invention

The present invention relates to an analyzer, an absorption characteristic calculation circuit, and an analysis method.

2. Description of the Related Art

A quantum cascade laser (QCL) is a laser that emits laser light having a wavelength in a mid-infrared range of 3 μm to 20 μm, for example. The QCL is highly expected as a small-sized and low-cost light source in various fields such as environmental gas analysis, medical diagnosis, and industrial processing. T. K. Subramaniam, "Quantum Cascade Laser in Atmospheric Trace Gas Analysis", AASCIT Journal of Environment, April 2015, discloses a technique of analyzing components of environmental gas by irradiating the gas with mid-infrared light emitted from the QCL, and by measuring a spectrum of the light having passed through the gas. Jonas Kottmann et al., "Mid-Infrared Photoacoustic Detection of Glucose in Human Skin: Towards Non-Invasive Diagnostics", Sensors, October 2016, discusses a feasibility of non-invasive diagnosis of a blood glucose value by utilizing absorption characteristics of glucose, etc. with respect to light of a particular wavelength in the mid-infrared range.

Other references are as follows:
Jane Hodgkinson and Ralph P Tatam, "Optical gas sensing: a review", Measurement Science and Technology, 24 (2013)
Lionel Tombez, "Analysis and improvement of the spectral properties in mid-infrared semiconductor quantum cascade lasers", doctoral thesis, UNIVERSITÉ DE NEUCHÂTEL, 2014
Andreas Hangauer et al., "High-speed Modulation Characteristic of a Quantum Cascade Laser", Conference Paper, ResearchGate, June 2013

SUMMARY OF THE INVENTION

In order to measure components of a gas sample and their concentrations, an absorption spectrum of the gas sample needs to be measured with high accuracy. For that purpose, a wavelength of mid-infrared light used in measurement needs to be changed accurately and continuously. It deems that the wavelength of the light emitted from the QCL can be changed by changing a temperature of the QCL with a thermoelectric cooler (TEC), and/or by changing an amount of injection current applied to the QCL. The following methods are known, by way of example. (a) According to one method, mid-infrared light changing in intensity and wavelength of the light is obtained by changing each of the temperature, the amount of injection current, and the length of a cavity formed by a reflective mirror disposed in the outside slowly to such an extent as maintaining a state in which a continuous wave of light is stably laser-oscillated from the QCL. (b) According to another method, the intensity of mid-infrared light with wavelength slowly changing in a stable laser oscillation state is changed by causing the light to pass through a chopper. (c) According to still another method, mid-infrared light changing in intensity and wavelength is obtained by modulating conditions of current injection to the QCL at a short time cycle.

With the above method (a), the wavelength of the light for use in measurement is stabilized, but a measurement time is prolonged. Another problem is that, with an increase of the measurement time, the influences of 1/f noise and drift caused in the QCL appear significantly and an S/N ratio decreases. With the above method (b), the influences of the drift, etc. can be reduced while the wavelength of the light is stabilized. However, there is a risk in regards to reliability and measurement accuracy because the mechanically-operated chopper is used.

With the above method (c), because the intensity of the light is electrically changed, the risk in regards to reliability is less in comparison with the above method (b). Furthermore, since the measurement can be performed in a shorter time than in the case of using the above method (a), the influences of the drift, etc. can be reduced. However, when the injection current to the QCL is changed at a short time cycle, a complicated wavelength shift from the expected wavelength change occurs due to the influence of frequency chirping and the influence of a temperature change of the QCL caused by a current change. In order to measure the absorption spectrum of the sample gas with high accuracy, it is desired to exclude the influence of the wavelength shift caused by the cyclic change of the injection current to the QCL as far as possible. Moreover, various conditions for the current injection are set on the QCL in order to measure a variety of gas samples having unknown components and concentrations. Because the wavelength shift changes depending on the conditions for the current injection, measuring the wavelength shifts under the various conditions for the current injection in advance takes a lot of effort and time.

To solve the above-described problem, an analyzer according to an embodiment includes an QCL that receives a driving signal including a cyclic waveform and converts the driving signal to laser light in a mid-infrared range, an optical receiver that receives the laser light having passed through a sample and outputs a detected signal depending on the intensity of the laser light, and a data calculation portion that outputs, on the basis of the detected signal, information representing absorption characteristics of the sample. The data calculation portion includes a delaying unit that produces a time-delayed waveform by applying, to one of a waveform of a reference driving signal and a waveform of the detected signal, a time delay in comparison with the other waveform, an adding unit that produces a symmetrical waveform by adding the time-delayed waveform to the other waveform, a time inversion unit that produces a time-inverted waveform by inverting a time dependency of the symmetrical waveform, and a subtracting unit that produces a waveform of a difference between the time-inverted waveform and the symmetrical waveform. The data calculation portion repeatedly calculates the waveform of the difference while the time delay applied in the delaying unit is changed, and outputs, as the information representing absorption characteristics of the sample, the symmetrical waveform or information obtained from the symmetrical waveform when an absolute value of the waveform of the difference is minimized.

An absorption characteristic calculation circuit according to an embodiment is to output information representing absorption characteristics of a sample on the basis of a detected signal depending on the intensity of laser light in a mid-infrared range, the laser light being generated in accordance with a driving signal including a cyclic waveform and passing through the sample. The absorption characteristic calculation circuit includes a delaying unit that produces a time-delayed waveform by applying, to one of a waveform of a reference driving signal and a waveform of the detected signal, a time delay in comparison with the other waveform, an adding unit that produces a symmetrical waveform by adding the time-delayed waveform and the other waveform, a time inversion unit that produces a time-inverted waveform by inverting the time dependency of the symmetrical waveform, and a subtracting unit that produces a waveform of a difference between the time-inverted waveform and the symmetrical waveform. The absorption characteristic calculation circuit repeatedly calculates the waveform of the difference while the time delay applied in the delaying unit is changed, and outputs, as the information representing the absorption characteristics of the sample, the symmetrical waveform or information obtained from the symmetrical waveform when an absolute value of the waveform of the difference is minimized.

An analysis method according to an embodiment includes a light generation step of supplying a driving signal including a cyclic waveform to a QCL, and converting the driving signal to laser light in a mid-infrared range, a light detection step of producing a detected signal depending on the intensity of the laser light that has passed through a sample, and a data calculation step of producing, on the basis of the detected signal, information representing absorption characteristics of the sample. The data calculation step includes a delaying step of applying, to one of a waveform of a reference driving signal and a waveform of the detected signal, a time delay in comparison with the other waveform, an adding step of producing a symmetrical waveform by adding the one time-delayed waveform and the other waveform, a time inversion step of producing a time-inverted signal by inverting a time dependency of the symmetrical waveform, and a subtracting step of producing a waveform of a difference between the time-inverted waveform and the symmetrical waveform. In the data calculation step, the waveform of the difference is repeatedly calculated while the time delay applied in the delaying step is changed, and the symmetrical waveform or information obtained from the symmetrical waveform when an absolute value of the waveform of the difference is minimized is given as the information representing the absorption characteristics of the sample.

BRIEF DESCRIPTION OF THE DRAWINGS

FIG. 2A depicts a sinusoidal driving waveform.

FIG. 2B depicts a triangular driving waveform.

FIG. 2C depicts a semicircular driving waveform.

DESCRIPTION OF THE PREFERRED EMBODIMENTS

Description of Embodiment of Present Invention

Figure 1:
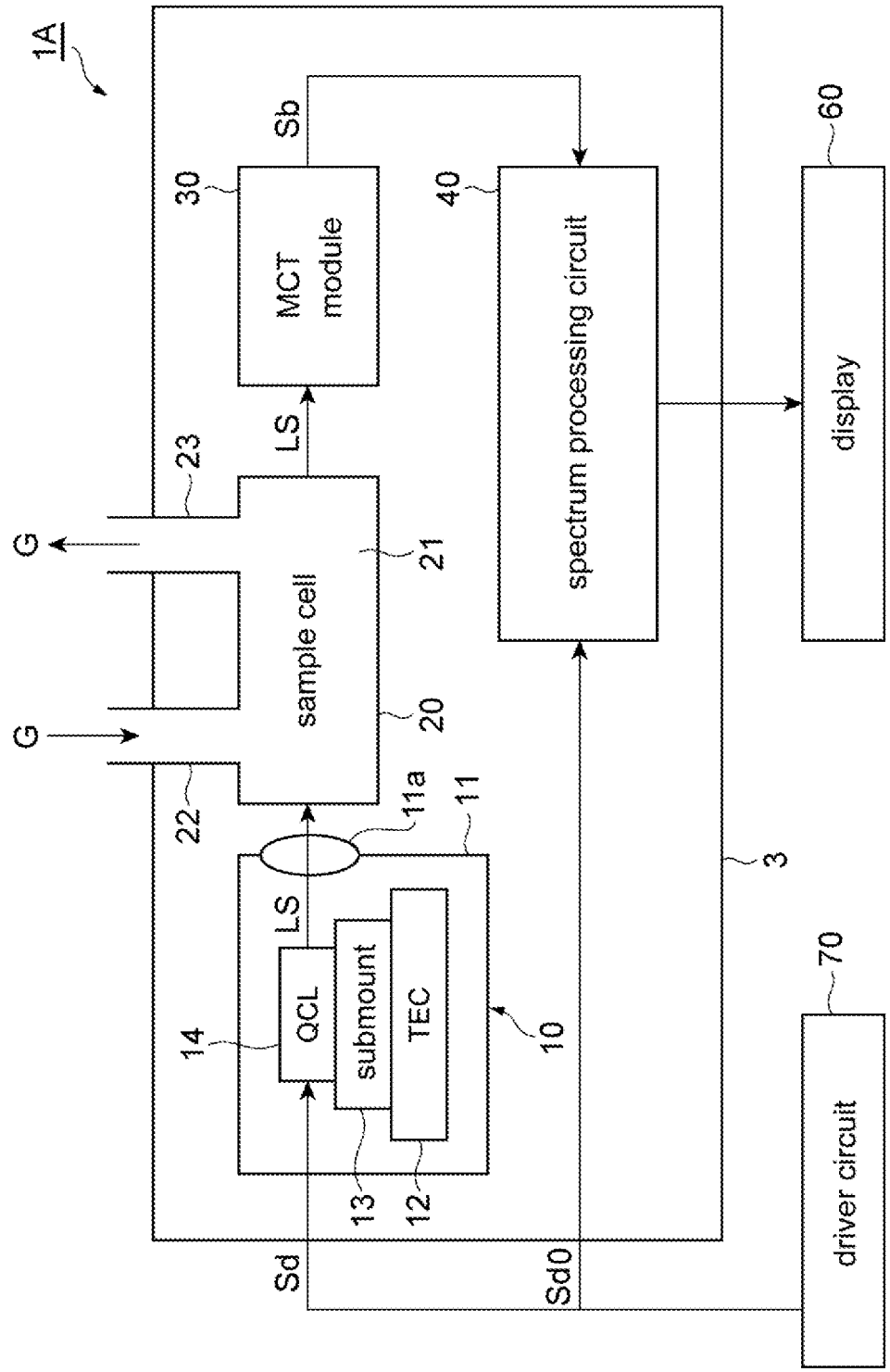
FIG. 1 is a block diagram illustrating a configuration of a gas analyzer that is an analyzer according to an embodiment of the present invention.

First, features of an embodiment of the present invention are described. An analyzer according to an embodiment includes an QCL that receives a driving signal including a cyclic waveform and converts the driving signal to laser light in a mid-infrared range, an optical receiver that receives the laser light having passed through a sample and outputs a detected signal depending on the intensity of the laser light, and a data calculation portion that outputs, on the basis of the detected signal, information representing absorption characteristics of the sample. The data calculation portion includes a delaying unit that produces a time-delayed waveform by applying, to one of a waveform of a reference driving signal and a waveform of the detected signal, a time delay in comparison with the other waveform, an adding unit that produces a symmetrical waveform by adding the time-delayed waveform and the other waveform, a time inversion unit that produces a time-inverted waveform by inverting a time dependency of the symmetrical waveform, and a subtracting unit that produces a waveform of a difference between the time-inverted waveform and the symmetrical waveform. The data calculation portion repeatedly calculates the waveform of the difference while the time delay applied in the delaying unit is changed, and outputs, as the information representing absorption characteristics of the sample, the symmetrical waveform or information obtained from the symmetrical waveform when an absolute value of the waveform of the difference is minimized.

An analysis method according to an embodiment includes a light generation step of supplying a driving signal including a cyclic waveform to a QCL, and converting the driving signal to laser light in a mid-infrared range, a light detection step of producing a detected signal depending on the intensity of the laser light that has passed through a sample, and a data calculation step of producing, on the basis of the detected signal, information representing absorption characteristics of the sample. The data calculation step includes a delaying step of applying, to one of a waveform of a reference driving signal and a waveform of the detected signal, a time delay in comparison with the other waveform, an adding step of producing a symmetrical waveform by adding the one time-delayed waveform and the other waveform, a time inversion step of producing a time-inverted signal by inverting a time dependency of the symmetrical waveform, and a subtracting step of producing a waveform of a difference between the time-inverted waveform and the symmetrical waveform. In the data calculation step, the waveform of the difference is repeatedly calculated while the time delay applied in the delaying step is changed, and the symmetrical waveform or information obtained from the symmetrical waveform when an absolute value of the waveform of the difference is minimized is given as the information representing the absorption characteristics of the sample.

According to the analyzer and the analysis method described above, the QCL receives the driving signal that is modulated so as to include the cyclic waveform. The QCL converts the driving signal to the laser light in the mid-infrared range where absorption wavelengths of many substances are present. The laser light is applied to the sample and passes through the sample while the laser light is partly absorbed at wavelengths corresponding to components of the sample. In the optical receiver (light detection step), the detected signal is produced depending on the intensity of the laser light that has passed through the sample. In the data calculation portion (data calculation step), the detected signal is processed, and the information representing the absorption characteristics of the sample is produced. A measurement operator can recognize the components of the sample and their concentrations on the basis of the produced information.

Furthermore, according to the analyzer and the analysis method described above, the data calculation portion (data calculation step) includes the delaying unit (delaying step), the adding unit (adding step), and the subtracting unit (subtracting step). The delaying unit (delaying step) applies, to one of a waveform of the driving signal and a waveform of the detected signal, a time delay in comparison with the other waveform. A phase difference is thus generated between the driving signal and the detected signal. The adding unit (adding step) adds both the waveforms having the phase difference therebetween. The subtracting unit (subtracting step) produces a waveform of a difference between a waveform obtained by time-inverting a waveform after the addition and the waveform after the addition. The waveform of the difference is repeatedly calculated while the time delay is changed. With the above-described configuration, the time delay when the absolute value of the waveform of the difference is minimized represents the magnitude of a time shift in wavelength. Accordingly, the accurate wavelength at which the absorption has occurred can be recognized in consideration of the time delay when the absolute value of the waveform of the difference is minimized. Stated in another way, according to the analyzer and the analysis method described above, the influence of the wavelength shift, which is caused by cyclic change of an injection current to the QCL, can be eliminated, and the information regarding the absorption characteristics of the sample can be accurately extracted from the detected signal. As a result, the absorption characteristics of the sample can be obtained with high accuracy using the measurement method of modulating the injection current to the QCL.

In the analyzer and the analysis method described above, the data calculation unit (data calculation step) may further include a waveform correction unit (waveform correction step) that produces, using parameters prepared in advance and the waveform of the reference driving signal, a corrected waveform by superimposing a distortion on the waveform of the driving signal to provide the corrected waveform closer to a waveform of the laser light output from the QCL. With that feature, since the above-described processing can be performed in the data calculation unit (data calculation step) in consideration of a variation in the light intensity (i.e., a distortion of the waveform of the laser light) caused by temperature changes, the absorption characteristics of the sample can be obtained with higher accuracy.

In the analyzer and the analysis method described above, the cyclic waveform may be given by a sinusoidal wave. With that feature, the driving signal including the cyclic waveform can be easily produced.

An absorption characteristic calculation circuit according to an embodiment is to output information representing absorption characteristics of a sample on the basis of a detected signal depending on the intensity of laser light in a mid-infrared range, the laser light being generated in accordance with a driving signal including a cyclic waveform and passing through the sample. The absorption characteristic calculation circuit includes a delaying unit that produces a time-delayed waveform by applying, to one of a waveform of a reference driving signal and a waveform of the detected signal, a time delay in comparison with the other waveform, an adding unit that produces a symmetrical waveform by adding the time-delayed waveform and the other waveform, a time inversion unit that produces a time-inverted waveform by inverting the time dependency of the symmetrical waveform, and a subtracting unit that produces a waveform of a difference between the time-inverted waveform and the symmetrical waveform. The absorption characteristic calculation circuit repeatedly calculates the waveform of the difference while the time delay applied in the delaying unit is changed, and outputs, as the information representing the absorption characteristics of the sample, the symmetrical waveform or information obtained from the symmetrical waveform when an absolute value of the waveform of the difference is minimized.

The absorption characteristic calculation circuit includes, as in the data calculation portion of the above-described analyzer, the delaying unit, the adding unit, and the subtracting unit. Accordingly, the influence of the wavelength shift, which is caused by the cyclic change of the injection current to the QCL, can be eliminated, and the information regarding the absorption characteristics of the sample can be accurately extracted from the detected signal. As a result, the absorption characteristics of the sample can be obtained with high accuracy using the measurement method of modulating the injection current to the QCL.

Details of Embodiment of Present Invention

Practical examples of the analyzer, the absorption characteristic calculation circuit, and the analysis method according to the embodiment of the present invention will be described below with reference to the drawings. The present invention is not limited to those practical examples, and the present invention is purported to include all modifications that are equivalent in meaning to the scope of Claims, and that fall within the scope of Claims. In the following description, the same elements in the drawings are denoted by the same reference signs, and duplicate description of those elements is omitted. It is to be noted that, in the following description, the term "waveform" stands for time dependency of a signal.

FIG. 1 is a block diagram illustrating a configuration of a gas analyzer 1A that is an analyzer according to the embodiment of the present invention. As illustrated in FIG. 1, the gas analyzer 1A according to this embodiment includes a QCL module 10 serving as a light source, a sample cell 20 containing sample gas, i.e., a gas sample to be measured, a mercury-cadmium-telluride: HgCdTe (MCT) module 30 serving as an optical receiver, a spectrum processing circuit 40 serving as a data calculation portion, a driver circuit 70 driving the QCL module 10, and a display 60. Of those components, the QCL module 10, the sample cell 20, the MCT module 30, and the spectrum processing circuit 40 are accommodated in a common housing 3. Although the driver circuit 70 and the display 60 are disposed outside the housing 3 in the illustrated example, they may be disposed inside the housing 3. At least one of the QCL module 10, the sample cell 20, the MCT module 30, and the spectrum processing circuit 40 may be disposed outside the housing 3.

Figure 2A:
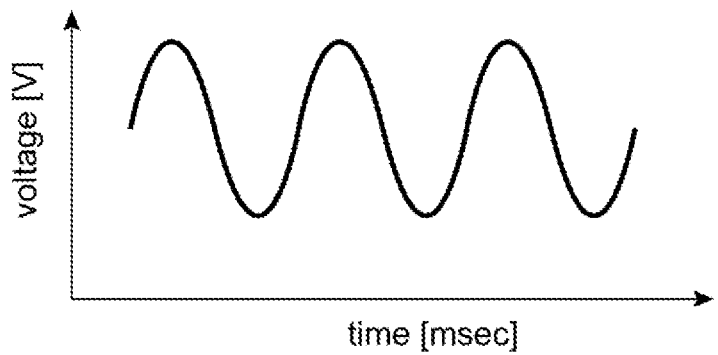
FIGS. 2A, 2B and 2C are graphs depicting various exemplary waveforms of a driving signal.
Figure 2B:
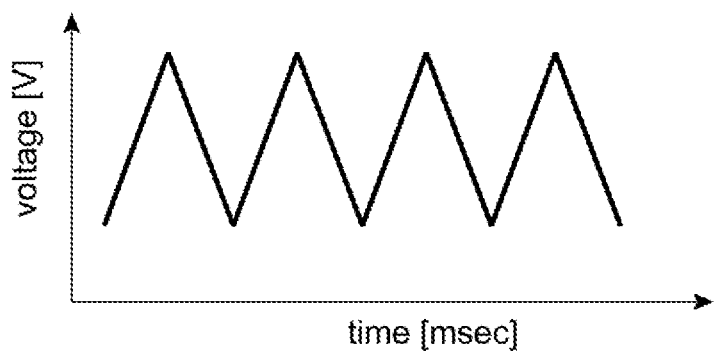
Figure 2C:
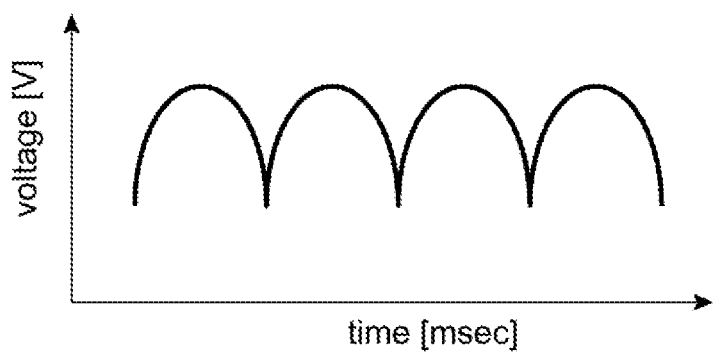

The driver circuit 70 is a circuit for producing an electrical driving signal Sd that is supplied to the QCL module 10. The driving signal Sd produced by the driver circuit 70 includes a cyclically changing voltage signal. A part of the driving signal is branched off from the driving signal Sd, and is sent to the spectrum processing circuit 40 as a reference driving signal Sd0. FIGS. 2A, 2B and 2C are graphs depicting various examples of time dependency of the driving signal Sd. FIG. 2A depicts a waveform of a signal with a voltage changing in the form of a sinusoidal wave at a certain time cycle. FIG. 2B depicts a waveform of a triangular wave signal with a voltage repeatedly increasing and decreasing in a linear form at a certain time cycle. FIG. 2C depicts a waveform of a signal with a voltage repeatedly increasing and decreasing in a semicircular form at a certain time cycle. Desirably, the time dependency of the driving signal Sd has time reversal symmetry in one cycle. Here, the term "time reversal symmetry" implies that, in a graph with a horizontal axis representing time, waveforms in time spans before and after a center time of one cycle are linearly symmetrical to each other. The driving signal Sd has a frequency of not less than 10 Hz and not more than 1 MHz, for example. The gas analyzer 1A may be supplied with the driving signal Sd from the outside of the gas analyzer 1A without including the driver circuit 70. The driving signal Sd0 has the same waveform as the driving signal Sd.

The QCL module 10 receives the driving signal Sd supplied from the driver circuit 70 and outputs laser light LS in a mid-infrared range. The QCL module 10 includes a package 11, a TEC 12, a submount 13, and a QCL 14. The package 11 air-tightly seals off the TEC 12, the submount 13, and the QCL 14. An exit window 11a is formed in part of the package 11. The exit window 11a is made of a material transparent to the wavelength of the laser light LS. The laser light LS produced inside the package 11 is emitted to the outside of the package 11 through the exit window 11a.

The QCL 14 is dynamically and sinusoidally driven upon receiving the driving signal Sd, and converts the driving signal Sd to the laser light LS in the mid-infrared range. In more detail, a current corresponding to the magnitude of a voltage of the driving signal Sd is injected to the QCL 14, and the QCL 14 is laser-oscillated by the injected current. A wavelength of the laser light output from the QCL 14 is longer than 3 μm and more preferably longer than 4 μm, for example. In addition, the wavelength of the laser light output from the QCL 14 is shorter than 10 μm and more preferably shorter than 8 μm, for example. Within such a wavelength range, the QCL 14 enables the laser oscillation wavelength to be changed over a range of about 0.01 μm (wavelength sweep) depending on change of the magnitude of the injection current. A spectrum width of the laser oscillation light from the QCL 14 when not subjected to the wavelength sweep is very narrow. Static characteristics of the QCL 14, i.e., changes of the intensity and the wavelength of the light from the QCL 14 with respect to the injection current when the injection current is statically changed, are previously measured and known.

The submount 13 is a rectangular parallelepiped member on which the QCL 14 is mounted. The submount 13 contains a material having good thermal conductivity, such as AlN. The QCL 14 is fixed onto a front surface of the submount 13 with, for example, a solder or a thermally conductive adhesive interposed between them. The QCL 14 generates heat due to the current injection, and the heat generated from the QCL 14 dissipates to the submount 13. The TEC 12 is placed on a bottom surface of the package 11. The submount 13 is mounted onto a stage of the TEC 12. The TEC 12 dissipates heat of the submount 13 to the package 11 upon receiving a driving current supplied from the outside of the package 11. The magnitude of the driving current supplied to the TEC 12 is controlled such that a temperature of the QCL 14 is kept constant. The temperature of the QCL 14 is not lower than 0° C. and not higher than 40° C., for example. The temperature of the QCL 14 is detected using a thermistor (not illustrated) that is arranged near the QCL 14, and a detected result is fed-back to the driving current of the TEC 12.

The sample cell 20 has a light entry window optically coupled to the QCL module 10, and a light exit window positioned opposite to the light entry window. The sample cell 20 further has a space 21 containing sample gas G, the space 21 being communicated with an inlet port 22 and an outlet port 23. The sample gas G is introduced into the space 21 through the inlet port 22 from the outside of the gas analyzer 1A. Moreover, the sample gas G is discharged to the outside of the gas analyzer 1A from the space 21 through the outlet port 23. In a box-like member defining the space 21, at least the light entry window and the light exit window are each made of a material transparent to the wavelength of the laser light LS. The laser light LS output from the QCL module 10 is applied to the sample gas G in the space 21 after passing through the light entry window. The laser light LS is absorbed at a wavelength corresponding to a certain component in the sample gas G. An amount by which the laser light LS is absorbed depends on a concentration of the relevant component in the sample gas G. After passing through the sample gas G while being absorbed, the laser light LS penetrates the light exit window and then goes to the outside of the space 21. The gas analyzer 1A may have a structure of emitting the laser light LS to an external space without including the sample cell 20.

The MCT module 30 receives the laser light LS having passed through the sample gas G, and outputs a detected signal Sb with a voltage depending on the intensity of the laser light LS that has reached the MCT module 30. The amplitude of the detected signal Sb depends on an amount by which the laser light LS is absorbed by the sample gas G. The MCT module 30 is optically coupled to the light exit window of the sample cell 20. The MCT module 30 includes a semiconductor MCT detector and has sensitivity in a wavelength range of 2 μm to 10 μm, for example. The MCT module 30 may further include a cooler for cooling the MCT detector to the temperature of liquid nitrogen, and an amplifier for amplifying a voltage output from the MCT detector and producing the detected signal Sb. The laser light LS having entered the MCT module 30 is converted to the detected signal Sb in the MCT detector.

Figure 3A:
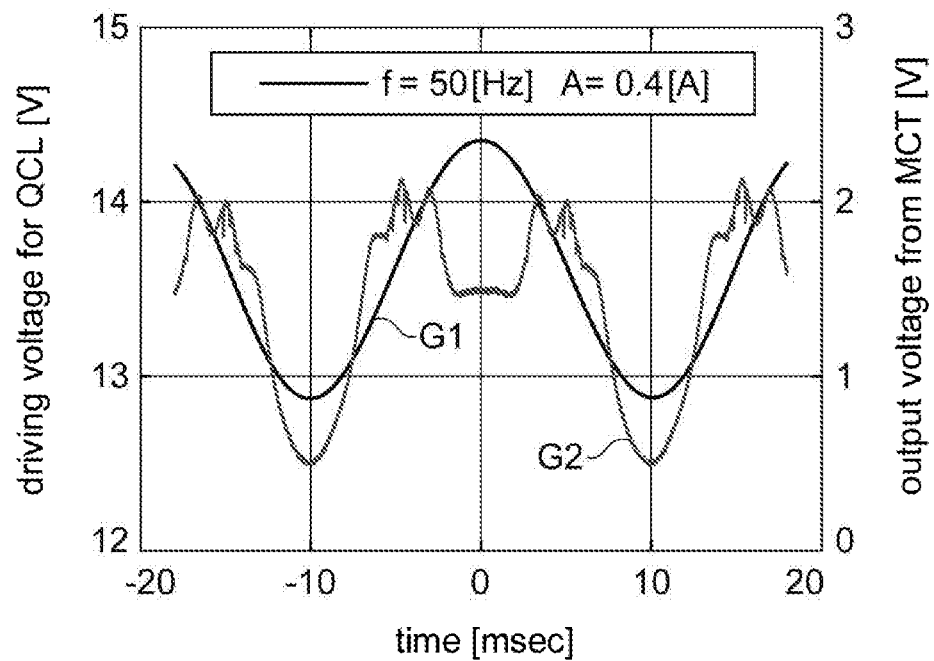
FIG. 3A is a graph depicting exemplary waveforms of the driving signal and a detected signal when a frequency of the driving signal is set to 50 Hz.
Figure 3B:
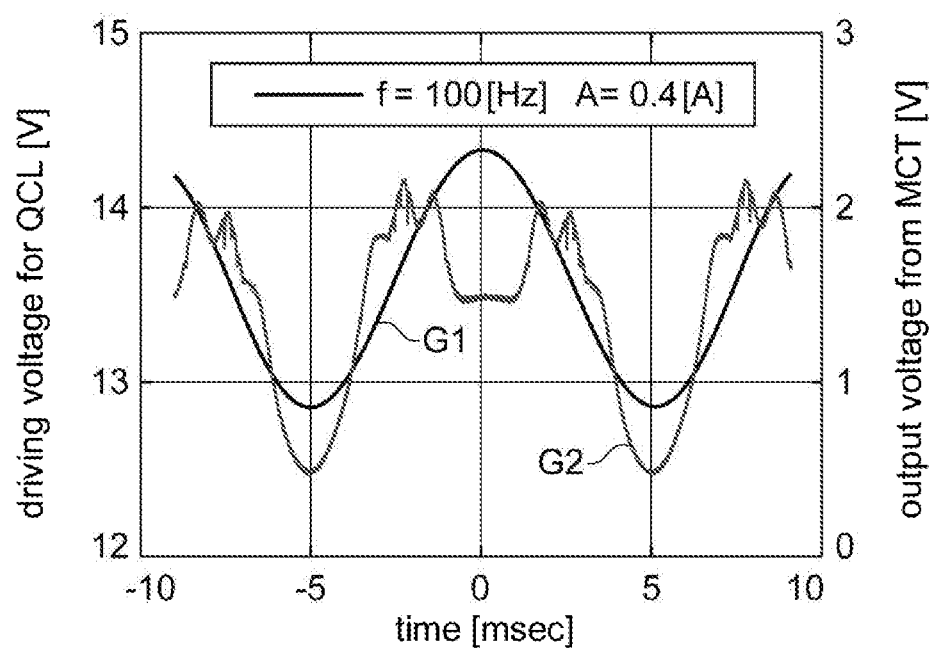
FIG. 3B is a graph depicting exemplary waveforms of the driving signal and the detected signal when the frequency of the driving signal is set to 100 Hz.
Figure 4A:
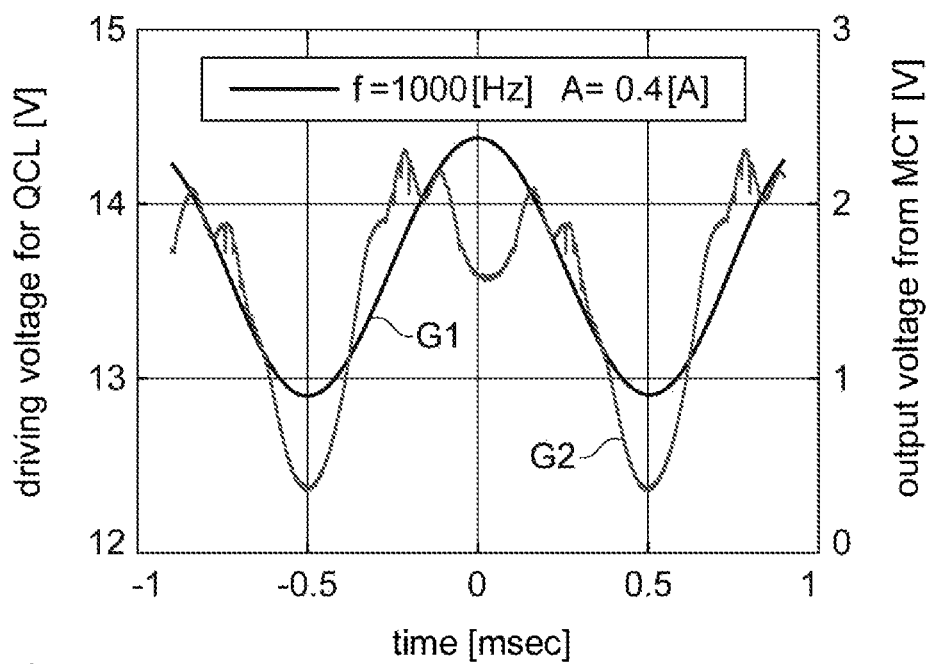
FIG. 4A is a graph depicting exemplary waveforms of the driving signal and the detected signal when the frequency of the driving signal is set to 1 kHz.
Figure 4B:
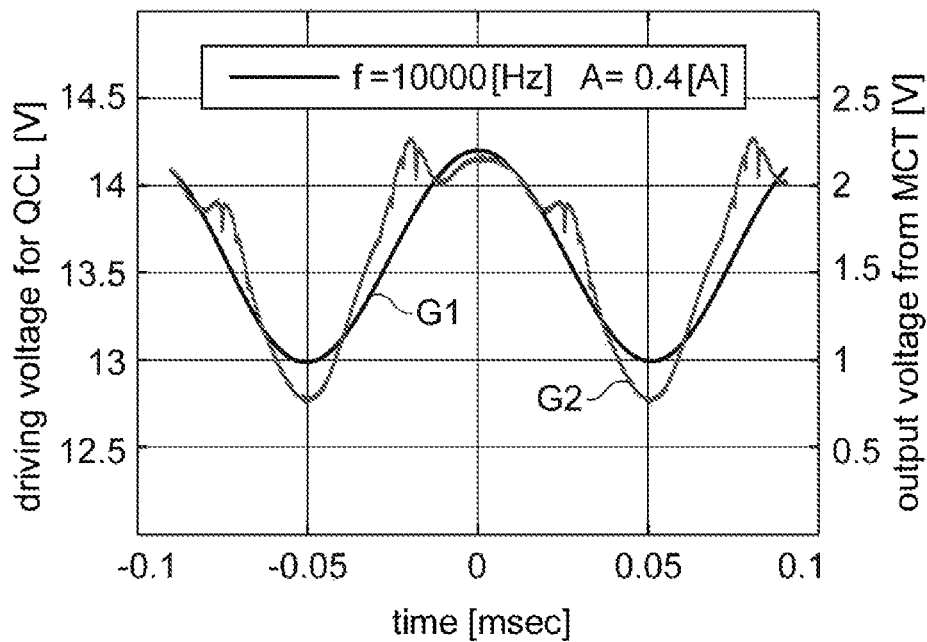
FIG. 4B is a graph depicting exemplary waveforms of the driving signal and the detected signal when the frequency of the driving signal is set to 10 kHz.

FIGS. 3A, 3B, 4A and 4B are each a graph depicting exemplary waveforms of the driving signal Sd and the detected signal Sb. In FIGS. 3A, 3B, 4A and 4B, a graph G1 represents a waveform of the driving signal Sd, and a graph G2 represents a waveform of the detected signal Sb. In the depicted examples, the waveform of the driving signal Sd has a sinusoidal shape. A horizontal axis indicates time (unit: msec), while a vertical axis on the left indicates a voltage value of the driving signal Sd (i.e., a voltage applied to the QCL 14, unit: V) and a vertical axis on the right indicates a voltage value of the detected signal Sb (i.e., a voltage output from the MCT detector, unit: V). FIGS. 3A and 3B represent respectively the cases in which the frequency of the driving signal Sd is set 50 Hz and 100 Hz. FIGS. 4A and 4B represent respectively the cases in which the frequency of the driving signal Sd is set 1 kHz and 10 kHz. A center voltage of the driving signal Sd is 13.7 (V), and a voltage amplitude is 1.5 (V). A peak-to-peak value of the driving current flowing in the QCL 14 is 0.4 (A) in each case.

As seen from FIGS. 3A, 3B, 4A and 4B, the waveform of the detected signal Sb is greatly distorted in comparison with that of the sinusoidal driving signal Sd. Such a distortion includes not only a reduction of the signal due to the absorption of the laser light by the sample gas G, but also influences of changes in the intensity and the wavelength of the laser light LS, which are caused by changing the driving signal Sd supplied to the QCL 14. More specifically, when the driving signal Sd is supplied to the QCL 14, the intensity of the laser light LS increases in proportion to the driving current that is in proportion to the driving signal Sd. On the other hand, the temperature of the QCL 14 rises with the supply of the driving current, and such a temperature rise reduces the light intensity. The wavelength of the laser light LS also changes in a similar manner. Thus, when the driving current increases, the wavelength of the laser light LS is prolonged. On the other hand, the temperature of an active layer in the QCL 14 rises, and this temperature rise shortens the wavelength. In addition, a temperature change of the active layer in the QCL 14 is delayed in time relative to a change of the driving current. Accordingly, when the driving signal Sd having the cyclic waveform is supplied to the QCL 14, the changes of the light intensity and wavelength caused by the temperature rise are superimposed in a delayed relation on the changes of the light intensity and wavelength caused by the change of the driving current. Therefore, the light intensity and wavelength change in a complicated way. In addition, a magnitude and a delay time of the temperature change of the QCL 14 further depend on the heat capacities of both the submount 13 onto which the QCL 14 is mounted and the TEC 12, and the ambient temperature of the gas analyzer 1A. For that reason, it is difficult to accurately estimate the magnitude and the delay time of the temperature change of the QCL. Moreover, as seen from FIGS. 3A, 3B, 4A and 4B, as the frequency of the driving signal Sd increases, the influence of the delay of the temperature change appears more significantly, and a distortion of the wavelength of the detected signal Sb increases. From the viewpoint of shortening the measurement time, it is preferable that the frequency of the driving signal Sd is as high as possible.

In consideration of the above-described point, in this embodiment, the spectrum processing circuit 40 described below excludes the influences of the changes of the light intensity and wavelength, which are caused by the change of the driving current supplied to the QCL 14, and extracts only absorption characteristics of the sample gas G. As illustrated in FIG. 1, the spectrum processing circuit 40 is electrically connected to the MCT module 30, and it receives the detected signal Sb from the MCT module 30. The spectrum processing circuit 40 then outputs, on the basis of the detected signal Sb, information representing the absorption characteristics of the sample gas G. The spectrum processing circuit 40 may be implemented with an analog and/or digital electronic circuit, for example. Alternatively, the spectrum processing circuit 40 may be implemented with a computer that includes a CPU and a memory, and that is operated by executing a predetermined program. The information representing the absorption characteristics of the sample gas G is output to a display 60 from the spectrum processing circuit 40, and is displayed on the display 60. A measurement operator can analyze gas components of the sample gas G on the basis of the information displayed on the display 60.

Figure 5:
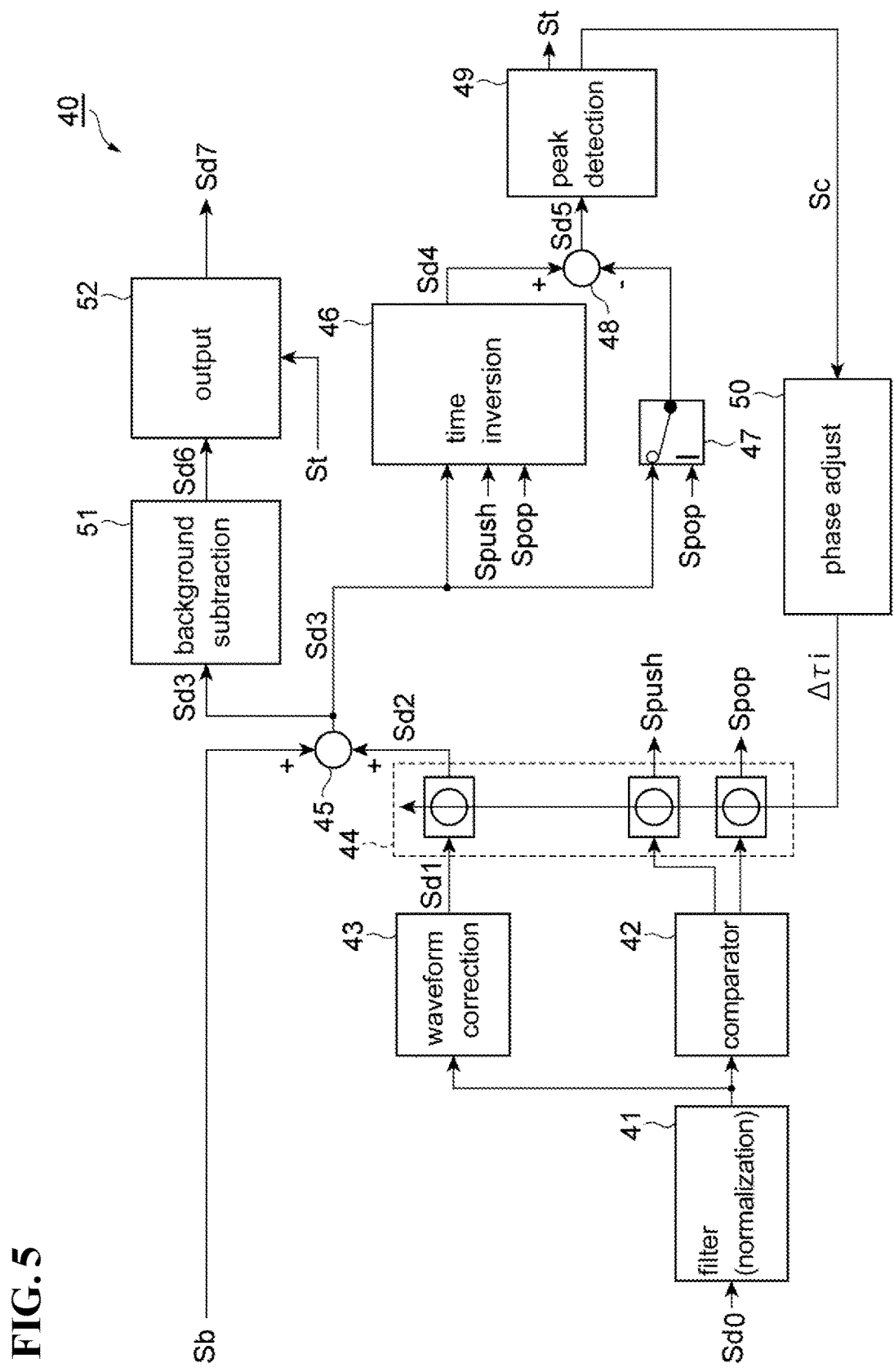
FIG. 5 is a block diagram illustrating an exemplary configuration of a spectrum processing circuit.

A practical exemplary configuration of the spectrum processing circuit 40 will be described below. FIG. 5 is a block diagram illustrating the exemplary configuration of the spectrum processing circuit 40. As illustrated in FIG. 5, the spectrum processing circuit 40 includes a filter circuit 41, a comparator circuit 42, a waveform correction circuit 43, a delaying circuit 44, an adding circuit 45, a time inverting circuit 46, a signal control circuit 47, a subtracting circuit 48, a peak detection circuit 49, a phase adjusting circuit 50, a background subtracting circuit 51, and an output circuit 52. Furthermore, the spectrum processing circuit 40 receives the detected signal Sb from the MCT module 30 and receives the reference driving signal Sd0 from the driver circuit 70. The spectrum processing circuit 40 uses the driving signal Sd0 in deciding a frequency of a corrected waveform given in the waveform correction circuit 43 described later, and in deciding a reference time to establish synchronization between the driving signal Sd0 and the corrected waveform. The driving signal Sd0 is introduced to the spectrum processing circuit 40 through, for example, a line branched from a wiring extending from the driver circuit 70 to the QCL module 10.

The filter circuit 41 performs filtering of the driving signal Sd0 and removes a noise component. The filter circuit 41 is constituted, for example, by a low pass filter including a resistance and a capacitor. Furthermore, the filter circuit 41 performs normalization of the driving signal Sd0 after the filtering. The term "normalization" stands for processing to adjust the amplitude of each input signal to be matched with a predetermined level. With the provision of the filter circuit 41, subsequent electrical processing steps performed by various circuits can be carried out with high accuracy. The filter circuit 41 may perform only one of the filtering and the normalization. Alternatively, the filter circuit 41 may be omitted. The driving signal Sd0 passing through the filter circuit 41 is sent to the comparator circuit 42 and the waveform correction circuit 43.

The waveform correction circuit 43 is a waveform correction unit in this embodiment, and it performs, using parameters prepared in advance, correction to make the waveform of the driving signal Sd0 closer to the waveform of the laser light LS output from the QCL 14. By way of example, the waveform correction circuit 43 produces, on the basis of the driving signal Sd0, a driving signal Sd1 that is a voltage signal having a primary corrected waveform δ(t) expressed by the following mathematical expression (1). The primary corrected waveform δ(t) is resulted from making the waveform of the driving signal Sd0 closer to the waveform of the laser light LS from the QCL 14 by superimposing a predetermined waveform distortion component on the driving signal Sd0.

$$\delta(t) = -h \cdot \sin \omega t \cdot \left\{ 1 - 4\alpha' \cdot \cos^2\left(\frac{\omega t}{2}\right) \right\} \quad (1)$$

Here, ω denotes a frequency extracted from the driving signal Sd0 by the waveform correction circuit 43. Furthermore, h and α' denote constants (parameters) of which initial values are input by the measurement operator in advance. Moreover, t denotes time. The mathematical expression (1) is based on a model representing that, when the driving signal Sd0 is sinusoidal, a delay of thermal response also becomes sinusoidal. The waveform distortion component in the mathematical expression (1) is determined by the constants h and α' related to the delay of thermal response. The constants h and α' are related to a delay time of the thermal characteristics and the magnitude of the temperature change of the QCL 14. Once the heat capacities of the QCL 14, the submount 13, and the TEC 12 inside the QCL module 10 are determined, values of h and α' are substantially determined incidental to those heat capacities. In the case of using the QCL modules 10 having the same configuration, the same values can be used as the initial values of h and α'. The waveform correction circuit 43 sends the produced driving signal Sd1 to the delaying circuit 44.

The delaying circuit 44 is a delaying unit in this embodiment, and it applies, to the waveform of the driving signal Sd1, a time delay in comparison with the waveform of the detected signal Sb. In other words, the delaying circuit 44 produces a driving signal Sd2 that is a voltage signal having a secondary corrected waveform δ(t−Δτ$_i$). Here, Δτ$_i$ denotes an i-th delay time (i=1, 2, etc.). The delay time Δτ$_i$ is set by the phase adjusting circuit 50, described later, in sequential order starting from i=1. The delaying circuit 44 sends the produced driving signal Sd2 to the adding circuit 45.

The adding circuit 45 is an adding unit in this embodiment. The adding circuit 45 adds the time-delayed driving signal Sd2 and the detected signal Sb, thereby producing a voltage signal Sd3 having a symmetrical waveform. The term "symmetrical waveform" stands for a waveform of the type that a waveform resulting from time-inverting an original waveform with respect to a certain point in time becomes the same as the original waveform. The adding circuit 45 sends the produced voltage signal Sd3 to the time inverting circuit 46, the signal control circuit 47, and the background subtracting circuit 51.

The above-described driving signal Sd0 output from filter circuit 41 is sent to the comparator circuit 42 as well. The comparator circuit 42 compares the magnitude of the driving signal Sd0 with a predetermined threshold, and produces a push signal Spush and a pop signal Spop. The produced push signal Spush and pop signal Spop are each delayed by the delaying circuit 44 through the same delay time Δτ$_i$ as that applied to the driving signal Sd1. The delayed push signal Spush is sent to the time inverting circuit 46. The delayed pop signal Spop is sent to the time inverting circuit 46 and the signal control circuit 47.

The time inverting circuit 46 is a time inversion unit in this embodiment, and it produces a voltage signal Sd4 having a time-inverted waveform using the waveform (symmetrical waveform) of the voltage signal Sd3 sent from the adding circuit 45. The time inverting circuit 46 inverts a time dependency of the voltage of the signal Sd3. More specifically, the time inverting circuit 46 produces the voltage signal Sd4 by repeatedly executing, on the voltage signal Sd3, a pushing process and a popping process in accordance with timings of the push signal Spush and the pop signal Spop with the aid of a Last In Last Out (LILO) buffer. The time inverting circuit 46 sends the produced voltage signal Sd4 after the time inversion to the subtracting circuit 48.

The signal control circuit 47 receives the voltage signal Sd3 from the adding circuit 45 and the delayed pop signal Spop from delaying circuit 44. The signal control circuit 47 sends the voltage signal Sd3 to the subtracting circuit 48 in accordance with timing of the pop signal Spop.

The subtracting circuit 48 is a subtracting unit in this embodiment. The subtracting circuit 48 calculates a difference between the voltage signal Sd3 and the voltage signal Sd4, thereby producing a voltage signal Sd5 having a waveform of the difference between the waveform of the voltage signal Sd3 and the waveform of the voltage signal Sd4. The voltage signal Sd5 represents an error value due to an inappropriate choice of the delay time Δτ$_i$. The subtracting circuit 48 sends the produced voltage signal Sd5 to the peak detection circuit 49.

The peak detection circuit 49 accumulates an absolute value of the waveform of the difference, which is included in the voltage signal Sd5, in a memory as a value corresponding to the delay time Δτ$_i$. The absolute value of the waveform of the difference represents an error value. The peak detection circuit 49 compares the present error value with each of the error values corresponding respectively to the delay times Δτ$_1$ to Δτ$_{i-1}$, which have been accumulated so far. If the delay time Δτ$_k$ (k is an integer of not smaller than 1 and not larger than i) at which the error value is minimized can be determined as a result of the comparison, the peak detection circuit 49 determines the relevant delay time Δτ$_k$ as the final delay time Δτ. The final delay time Δτ represents a phase shift in the wavelength of the laser light LS. In other words, assuming the delay time Δτ to be a reference time, the wavelength can be recognized on the basis of a time difference from the reference time. After determining the final delay time Δτ, the peak detection circuit 49 outputs a timing signal St. If the delay time Δτ at which the error value is minimized cannot be determined, the peak detection circuit 49 accumulates the relevant error value as the error value at the relevant delay time Δτ$_i$. Then, the peak detection circuit 49 sends, to the phase adjusting circuit 50, a signal Sc instructing generation of a next delay time Δτ$_{i+1}$. At that time, the phase adjusting circuit 50 generates the new delay time Δτ$_{i+1}$ different from the delay times Δτ$_1$ to Δτ$_i$, which have been generated so far, and sends the generated delay time to delaying circuit 44. The delaying circuit 44, the adding circuit 45, the time inverting circuit 46, the signal control circuit 47, the subtracting circuit 48, and the peak detection circuit 49 repeat the above-described operations until the delay time $\Delta\tau_k$ at which the error value is minimized can be determined. Stated in another way, the spectrum processing circuit 40 repeatedly calculates the waveform of the difference while the delay time $\Delta\tau_i$ applied in the delaying circuit 44 is changed.

The background subtracting circuit 51 is a filter for removing background noise that is included in the voltage signal Sd3 received from the adding circuit 45 and having the symmetrical waveform. The filter is a high pass filter, for example. The background subtracting circuit 51 sends, to the output circuit 52, a voltage signal Sd6 obtained after removing the background noise.

The output circuit 52 receives, from the background subtracting circuit 51, the voltage signal Sd6 obtained after removing the background noise, and further receives the timing signal St from the peak detection circuit 49. The output circuit 52 produces a voltage signal Sd7 having a waveform resulting from time-inverting the waveform of the voltage signal Sd6. Upon receiving the timing signal St sent from the peak detection circuit 49, the output circuit 52 outputs a voltage signal Sd7, as information (absorption spectrum) representing the absorption characteristics of the sample gas G, to the display 60 at the timing of receiving the timing signal St. In other words, the output circuit 52 outputs, as the information representing the absorption characteristics of the sample gas G, information (voltage signal Sd7) that is obtained from the symmetrical waveform (voltage signal Sd3) after the addition when the error value is minimized. The output circuit 52 may output directly the symmetrical waveform (voltage signal Sd3 or Sd6) after the addition when the error value is minimized, or may output different information (e.g., absorption wavelength data) that is obtained from the symmetrical waveform (the voltage signal Sd3) after the addition when the error value is minimized. The measurement operator can recognize the components of the sample gas G on the basis of the output information.

Figure 6A:
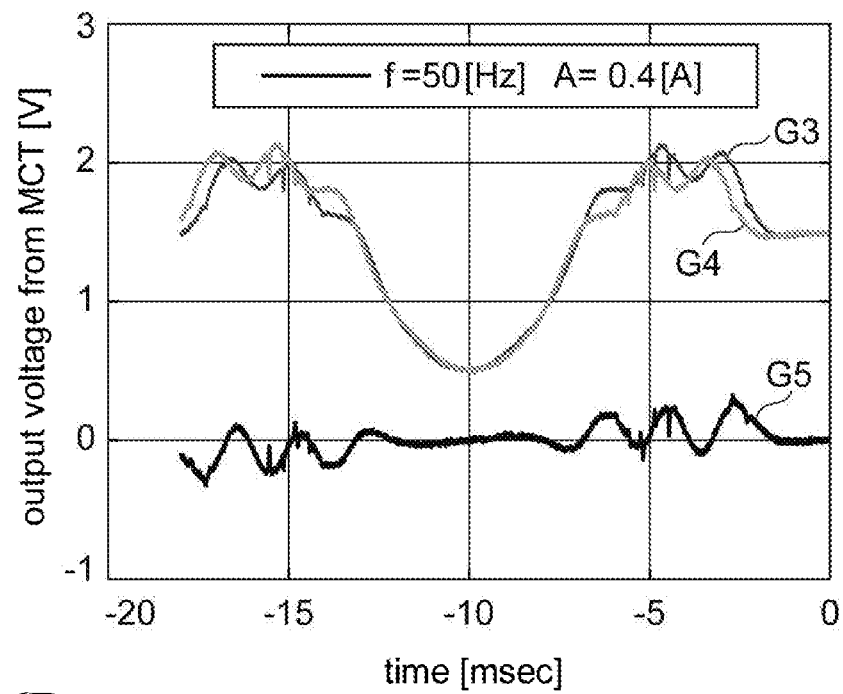
FIG. 6A depicts examples of a symmetrical waveform, a time reversal waveform, and an error value at a certain delay time when the frequency of the driving signal is set to 50 Hz.
Figure 6B:
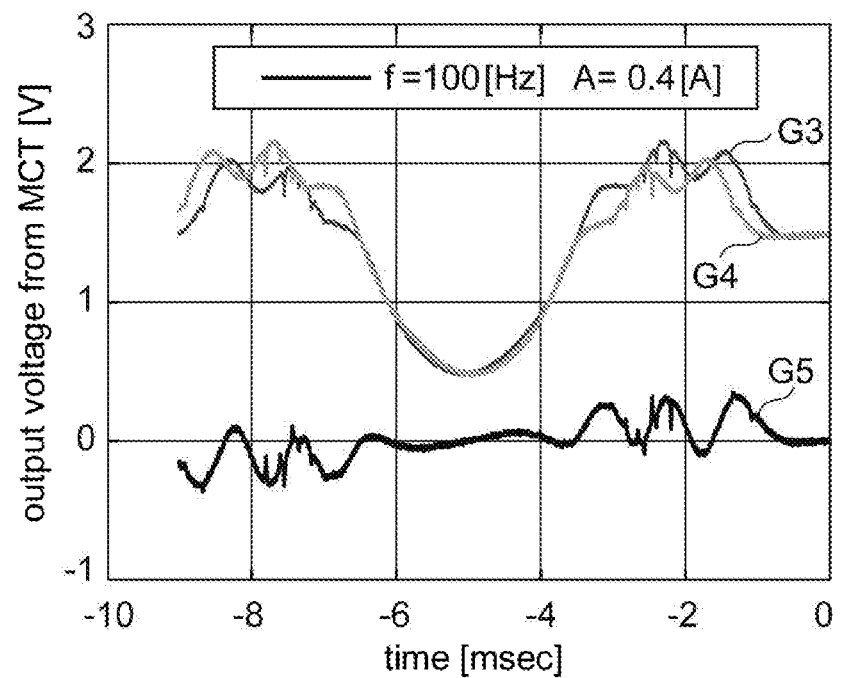
FIG. 6B depicts examples of the symmetrical waveform, the time reversal waveform, and the error value at a certain delay time when the frequency of the driving signal is set to 100 Hz.
Figure 7A:
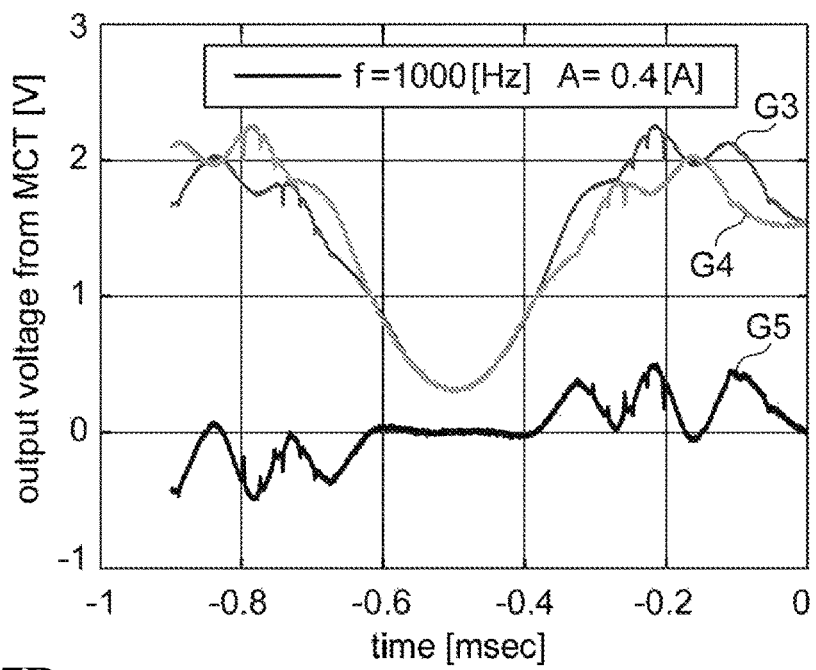
FIG. 7A depicts examples of the symmetrical waveform, the time reversal waveform, and the error value at a certain delay time when the frequency of the driving signal is set to 1 kHz.
Figure 7B:
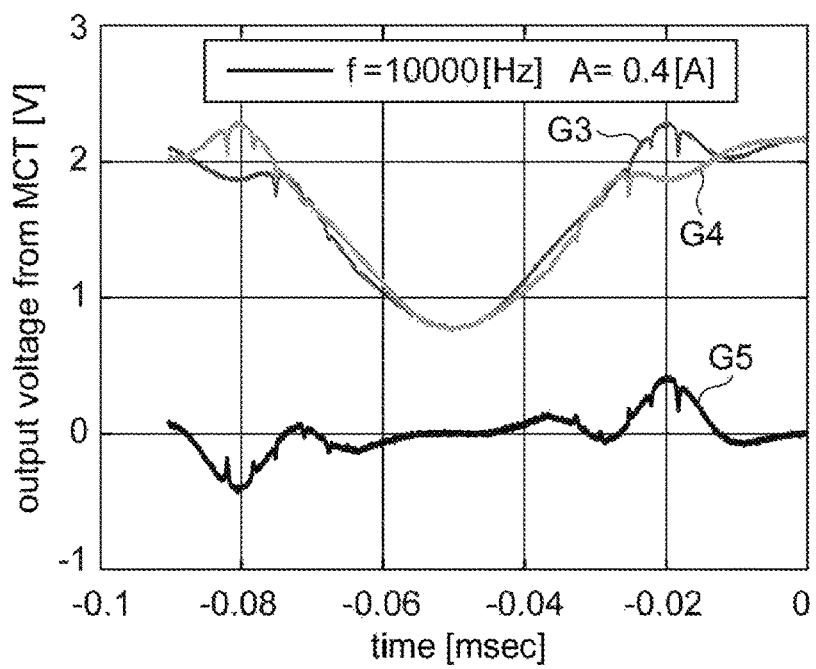
FIG. 7B depicts examples of the symmetrical waveform, the time reversal waveform, and the error value at a certain delay time when the frequency of the driving signal is set to 10 kHz.
Figure 8A:
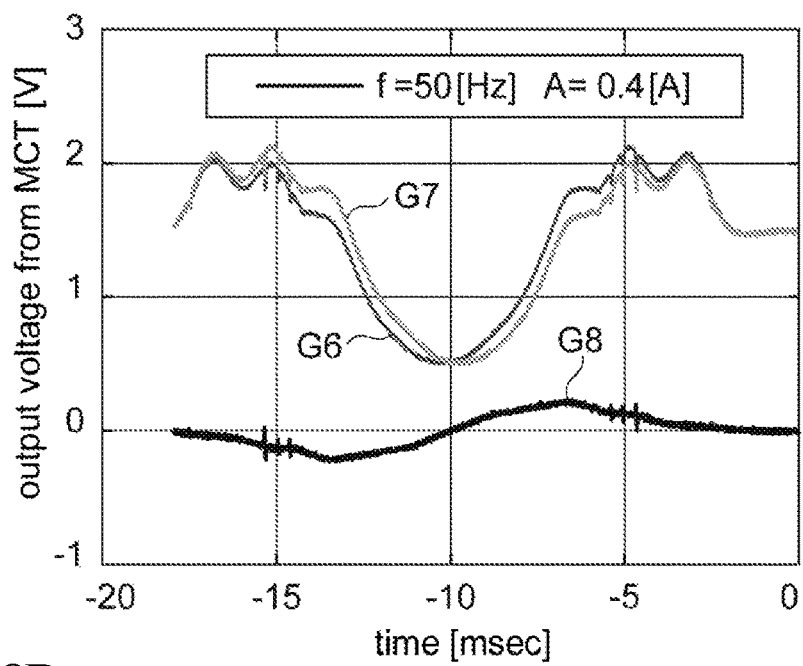
FIG. 8A depicts examples of the symmetrical waveform, the time reversal waveform, and the error value at an optimum delay time at which the error value is minimized, when the frequency of the driving signal is set to 50 Hz.
Figure 8B:
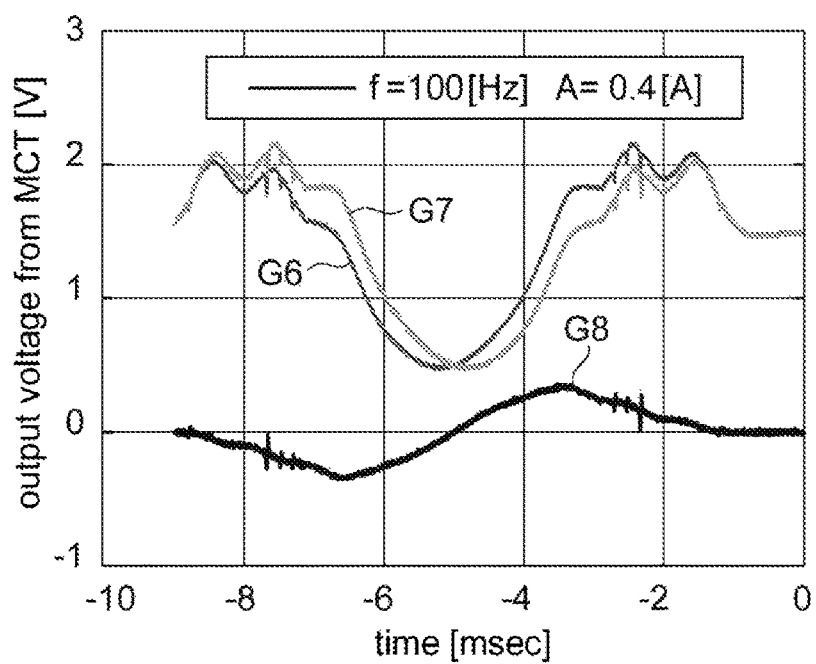
FIG. 8B depicts examples of the symmetrical waveform, the time reversal waveform, and the error value at the optimum delay time at which the error value is minimized, when the frequency of the driving signal is set to 100 Hz.
Figure 9A:
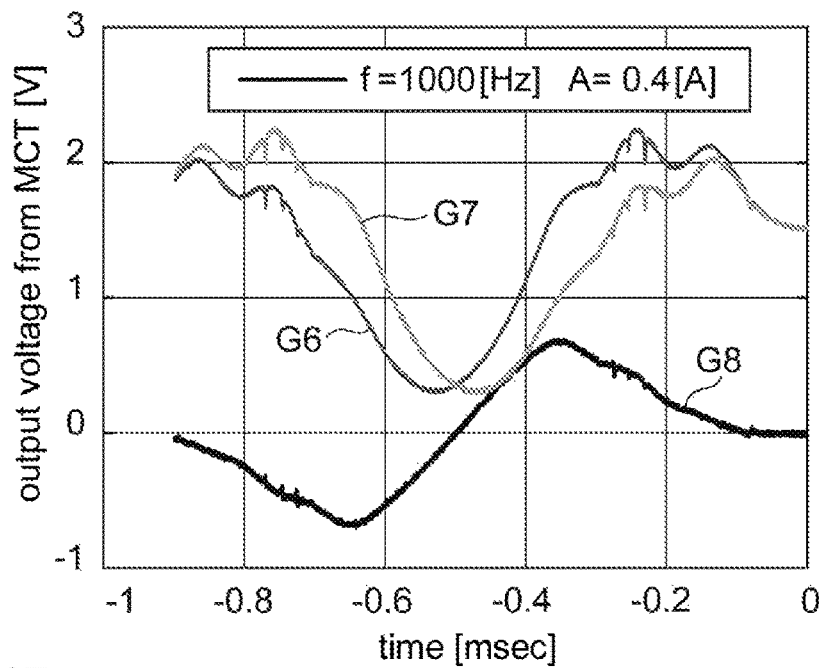
FIG. 9A depicts examples of the symmetrical waveform, the time reversal waveform, and the error value at the optimum delay time at which the error value is minimized, when the frequency of the driving signal is set to 1 kHz.
Figure 9B:
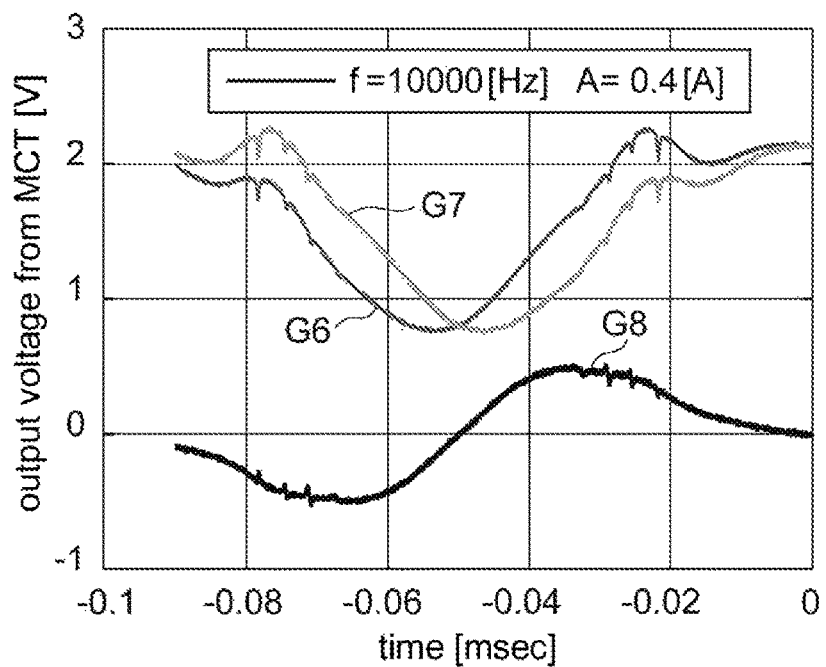
FIG. 9B depicts examples of the symmetrical waveform, the time reversal waveform, and the error value at the optimum delay time at which the error value is minimized, when the frequency of the driving signal is set to 10 kHz.

FIGS. 6A, 6B, 7A and 7B depict examples of the symmetrical waveform (graph G3) given by the voltage signal Sd3, the time-inverted waveform (graph G4) given by the voltage signal Sd4, and the error value (graph G5) given by the voltage signal Sd5 at a certain delay time $\Delta\tau_i$. FIGS. 8A, 8B, 9A and 9B depict examples of the symmetrical waveform (graph G6) given by the voltage signal Sd3, the time-inverted waveform (graph G7) given by the voltage signal Sd4, and the error value (graph G8) given by the voltage signal Sd5 at the optimum delay time $\Delta\tau_k$ at which the error value is minimized. In each of FIGS. 6A to 9B, a horizontal axis indicates time (unit: msec), and a vertical axis indicates a voltage value of the detected signal Sb (i.e., an output voltage from the MCT detector, unit: V). FIGS. 6A and 8A represent the cases in which the frequency of the driving signal Sd is set to 50 Hz. FIGS. 6B and 8B represent the cases in which the frequency of the driving signal Sd is set to 100 Hz. FIGS. 7A and 9A represent the cases in which the frequency of the driving signal Sd is set to 1 kHz. FIGS. 7B and 9B represent the cases in which the frequency of the driving signal Sd is set to 10 kHz.

Referring to FIGS. 6A to 9B, at the optimum delay time $\Delta\tau_k$ at which the error value is minimized, medium-cycle undulations in the error value (graph G8) are smaller than those (namely, the error value is smaller than that) in the case (graph G5) in which the delay time is not optimum. Thus, in the symmetrical waveform (graph G6), steep variations having very short cycles (i.e., variations attributable to absorption by the sample gas G) can be identified with high accuracy. Furthermore, long-cycle undulations (waves) in the error value (graph G8) can be reduced (namely, the graph G8 can be made closer to a flat line) by appropriately adjusting the parameters h and cc' in the mathematical expression (1) in the waveform correction circuit 43. Alternatively, the long-cycle undulations may be reduced using the background subtracting circuit 51.

Figure 10:
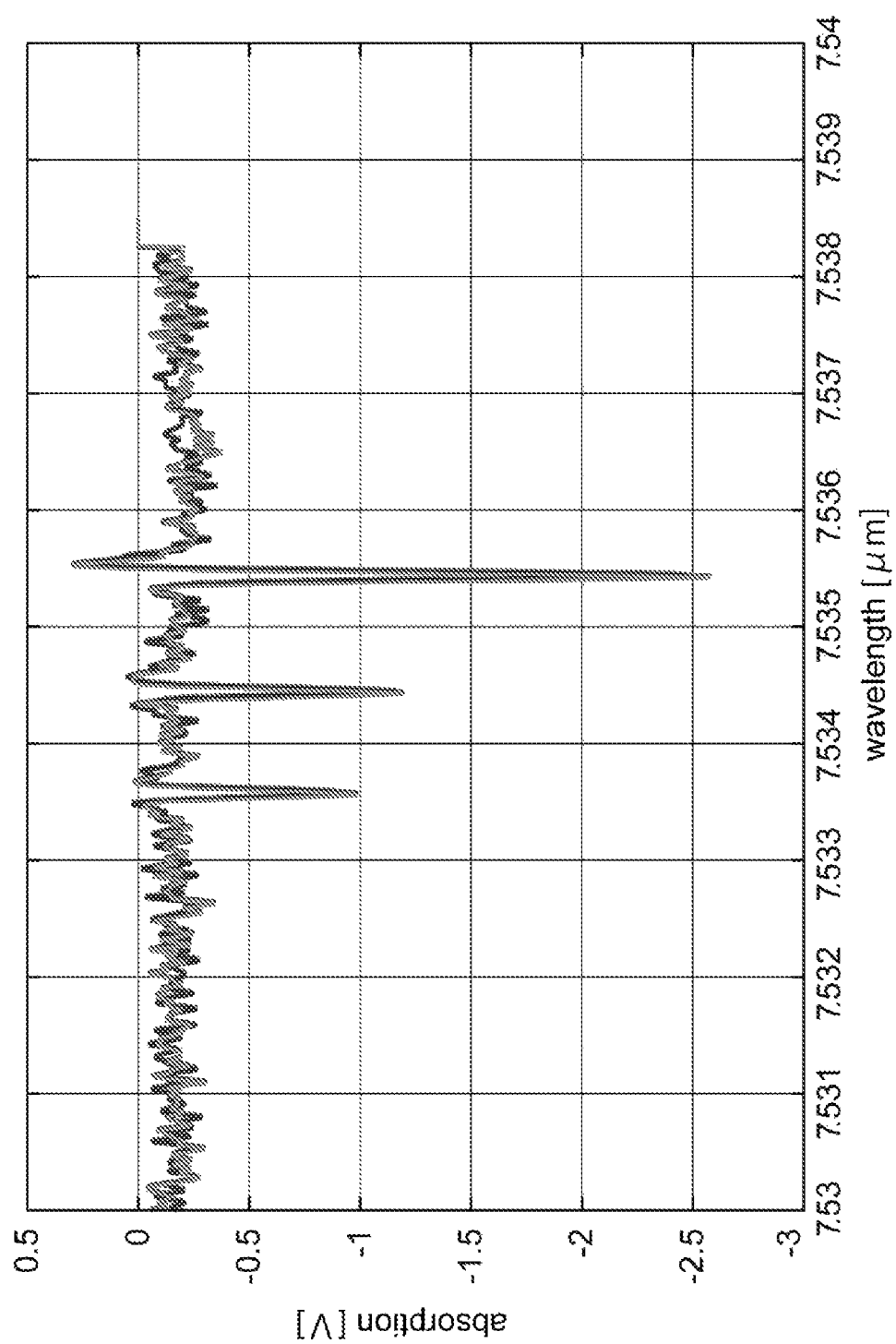
FIG. 10 is a graph depicting absorption characteristics (absorption spectrum) extracted from the symmetrical waveform after optimizing the delay time and removing long-cycle undulations.

FIG. 10 is a graph depicting absorption characteristics (absorption spectrum) extracted from the symmetrical waveform after optimizing the delay time $\Delta\tau$ and removing the long-cycle undulations. In FIG. 10, a horizontal axis indicates wavelength converted from time, and a vertical axis indicates voltage (unit: V) depending on an amount of light absorbed by the sample gas G. As seen from FIG. 10, sharp absorption peaks appear at certain wavelengths corresponding to components contained in the sample gas G. The components contained in the sample gas G can be recognized from both numerical values of those wavelengths and absorption intensities of individual peaks (i.e., magnitudes of the peaks).

Figure 11:
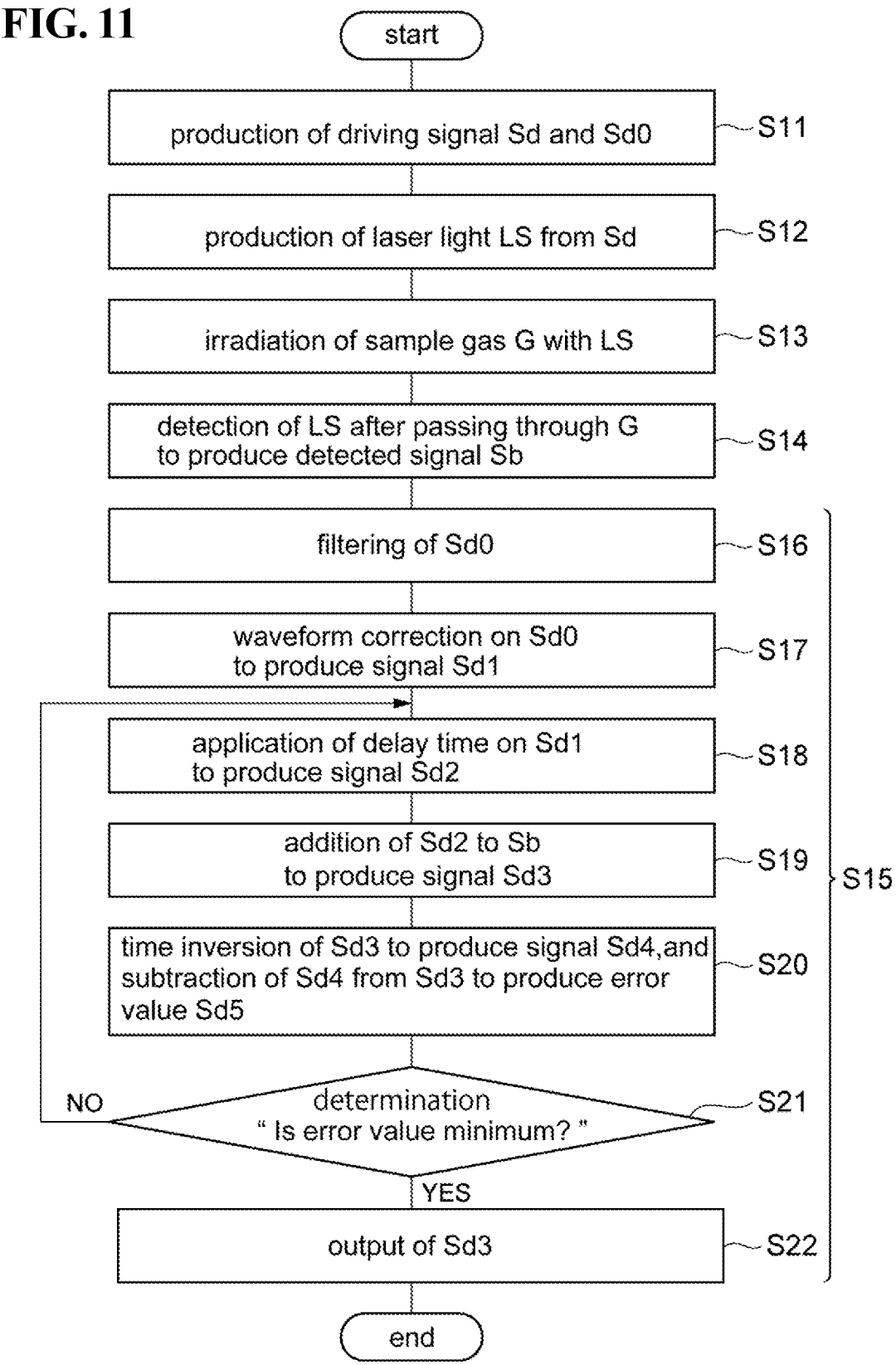
FIG. 11 is a flowchart representing individual steps of a gas analysis method.

A gas analysis method using the gas analyzer 1A according to this embodiment will be described below. FIG. 11 is a flowchart representing individual steps of the gas analysis method according to this embodiment. First, the driving signal Sd and Sd0 including the cyclic waveform is produced in the driver circuit 70 (signal production step S11). Then, the driving signal Sd is supplied from the driver circuit 70 to the QCL 14, and the driving signal Sd is converted to the laser light LS in the mid-infrared range (light production step S12). Then, the sample gas G in the sample cell 20 is irradiated with the laser light LS (irradiation step S13). Then, the detected signal Sb depending on the intensity of the laser light LS after passing through the sample gas G is produced in the MCT module 30 (light detection step S14).

Subsequently, in the spectrum processing circuit 40, the information representing the absorption characteristics of the sample gas G is produced on the basis of the detected signal Sb (data calculation step S15). The waveform of the driving signal Sd0 is used as a base waveform to be modified through the calculation steps. In the data calculation step S15, a filtering process is performed on the driving signal Sd0 in the filter circuit 41 (filtering step S16). Then, correction of the driving signal Sd0 is performed in the waveform correction circuit 43 such that the predetermined distortion is superimposed on the driving signal Sd0 to produce the driving signal Sd1 having the corrected waveform made closer to the waveform of the laser light LS from the QCL 14 (waveform correction step S17). Then, in the delaying circuit 44, the delay time $\Delta\tau$ in comparison with the waveform of the detected signal Sb is applied to the waveform of the driving signal Sd1 to produce the driving signal Sd2 (delaying step S18). Then, in the adding circuit 45, the waveform of the time-delayed driving signal Sd2 and the waveform of the detected signal Sb are added to produce the symmetrical waveform Sd3 (adding step S19). Then, the time inverting circuit 46 produces the waveform Sd4 resulting from time-inverting the symmetrical waveform Sd3 after the addition, and the subtracting circuit 48 produces a waveform Sd5 representing the difference between the time-inverted waveform Sd4 and the symmetrical waveform Sd3 (inversion and subtracting step S20). Then, the peak detection circuit 49 determines whether the absolute value of the waveform of the difference Sd5, i.e., the error value, is a minimum (determination step S21). If the error value is not a minimum (determination step S21: NO), the delay time $\Delta\tau$ in the delaying step S18 is changed to another delay time $\Delta\tau_i$, and the waveform of the difference Sd5 is obtained again by repeating the delaying step S18, the adding step S19, and the inversion and subtracting step S20. If the error value is a minimum (determination step S21: YES), the background noise is removed in the background subtracting circuit 51 from the symmetrical waveform after the addition, and the resulting symmetrical waveform is output from the output circuit 52 as the information representing the absorption characteristics of the sample gas G (output step S22).

The advantageous effects obtained with the above-described gas analyzer 1A and gas analysis method according to the embodiment will be described below. In one of methods for carrying out gas analysis with the use of the QCL, the wavelength and the intensity of the laser light are cyclically changed by modulating the injection current to the QCL. In such a method, however, the wavelength chirping of the QCL and the wavelength shift due to heating of the QCL (i.e., dynamic characteristics of the QCL) affect the signal detected by the MCT. On the other hand, in the gas analyzer according to this embodiment, only the absorption characteristics of the sample gas G are taken out in the spectrum processing circuit by subtracting the influence of the dynamic characteristics of the QCL 14 from the waveform of the detected signal Sb (in which the absorption characteristics of the sample gas G and the dynamic characteristics of the QCL 14 are mixed together).

More specifically, in the gas analyzer 1A and the analysis method according to the embodiment, the spectrum processing circuit 40 (data calculation step S15) includes, as described above, the delaying circuit 44 (delaying step S18), the adding circuit 45 (adding step S19), and the subtracting circuit 48 (subtracting step S20). The delaying circuit 44 (delaying step S18) applies, to the waveform of the driving signal Sd0, the delay time $\Delta\tau_i$ in comparison with the waveform of the detected signal Sb. A phase difference is thus generated between the driving signal Sd and the detected signal Sb. Then, the adding circuit 45 (adding step S19) adds both the waveforms having the phase difference to each other. Furthermore, the subtracting circuit 48 (subtracting step S20) produces the waveform of the difference between the waveform obtained by time-inverting the waveform after the addition, and the waveform after the addition (i.e., the symmetrical waveform). The waveform of the difference is repeatedly calculated while the delay time $\Delta\tau_i$ is changed.

In the above-described configuration, the delay time $\Delta\tau_k$ when the absolute value of the waveform of the difference is minimized represents the magnitude of a time shift in wavelength. Accordingly, the accurate wavelength at which the absorption has occurred can be recognized in consideration of the delay time $\Delta\tau_k$ when the absolute value of the waveform of the difference is minimized. Stated in another way, with the gas analyzer 1A and the gas analysis method according to this embodiment, the influence of the wavelength shift, which is caused by the cyclic change of the injection current to the QCL 14, can be eliminated, and the information regarding the absorption characteristics of the sample gas G can be accurately extracted from the detected signal Sb. As a result, the absorption characteristics of the sample gas G can be obtained with high accuracy in the measurement method of modulating the injection current to the QCL 14.

Furthermore, with the spectrum processing circuit 40 in the embodiment, since details of the processing are comparatively simple and the number of necessary circuits is relatively small, the spectrum processing circuit 40 can be constituted in a small size. Thus, the size of the housing 3 can be reduced, and portability of the analyzer can be increased.

Moreover, as in the embodiment, the spectrum processing circuit 40 (data calculation step S15) may include the waveform correction circuit 43 (waveform correction step S17) that corrects, using the parameters (h and α') prepared in advance, the waveform of the driving signal Sd to become closer to the waveform of the laser light LS output from the QCL 14. With that feature, since the above-described processing can be performed in the spectrum processing circuit 40 (data calculation step S15) in consideration of the variation in the light intensity (i.e., the distortion of the waveform of the laser light LS) caused by temperature changes, the absorption characteristics of the sample gas G can be obtained with higher accuracy. In addition, with the gas analyzer 1A according to this embodiment, since the number of parameters having arbitrary properties is small, namely just h and α', wavelength characteristics can be extracted with high reliability.

As in the embodiment, the cyclic waveform may be given by a sinusoidal wave. By using a sinusoidal wave, the driving signal Sd including the cyclic waveform can be easily produced. Furthermore, since the distortion of the waveform of the laser light LS can be expressed by a simple expression using trigonometric functions, such as the mathematical expression (1) in the embodiment, the number of parameters can be reduced.

The analyzer, the absorption characteristic calculation circuit, and the analysis method according to the present invention are not limited to the above-described embodiment, and they may be modified in various ways. For instance, while gas (gas sample) is used, by way of example, as the sample to be measured in the above-described embodiment, the present invention can be applied to a liquid or solid sample as well. Moreover, while, in the above-described embodiment, the delaying unit applies the time delay to the corrected waveform produced from the driving signal, the delaying unit may apply the time delay to the waveform of the detected signal because the purpose of the delaying unit is to apply a phase difference between the driving signal and the detected signal. Moreover, the corrected waveform given in the waveform correction unit is not limited to the waveform expressed by the mathematical expression (1) including the parameters (h and α'), a mathematical expression including other appropriate parameters may be used as required.

What is claimed is:
1. An analyzer comprising:
   a quantum cascade laser that receives a driving signal including a cyclic waveform and converts the driving signal to laser light in a mid-infrared range;
   an optical receiver that receives the laser light having passed through a sample and outputs a detected signal depending on intensity of the laser light; and
   a data calculation portion that outputs, on basis of the detected signal, information representing absorption characteristics of the sample,
   the data calculation portion including:
   a delaying unit that produces a time-delayed waveform by applying, to one of a waveform of a reference driving signal and a waveform of the detected signal, a time delay in comparison with the other waveform;
   an adding unit that produces a symmetrical waveform by adding the time-delayed waveform and the other waveform;

a time inversion unit that produces a time-inverted waveform by inverting a time dependency of the symmetrical waveform; and a subtracting unit that produces a waveform of a difference between the time-inverted waveform and the symmetrical waveform, wherein the data calculation portion repeatedly calculates the waveform of the difference while the time delay applied in the delaying unit is changed, and outputs, as the information representing absorption characteristics of the sample, the symmetrical waveform or information obtained from the symmetrical waveform when an absolute value of the waveform of the difference is minimized.

2. The analyzer according to claim 1, wherein the data calculation portion further comprises a waveform correction unit that produces, using parameters prepared in advance and the waveform of the reference driving signal, a corrected waveform by superimposing a distortion on the waveform of the driving signal to provide the corrected waveform closer to a waveform of the laser light output from the quantum cascade laser.

3. The analyzer according to claim 2, wherein the cyclic waveform is given by a sinusoidal wave.

4. An absorption characteristic calculation circuit of outputting information representing absorption characteristics of a sample on basis of a detected signal depending on intensity of laser light in a mid-infrared range, the laser light being generated in accordance with a driving signal including a cyclic waveform and passing through the sample, the absorption characteristic calculation circuit comprising:

a delaying unit that produces a time-delayed waveform by applying, to one of a waveform of a reference driving signal and a waveform of the detected signal, a time delay in comparison with the other waveform;

an adding unit that produces a symmetrical waveform by adding the time-delayed waveform and the other waveform;

a time inversion unit that produces a time-inverted waveform by inverting the time dependency of the symmetrical waveform; and a subtracting unit that produces a waveform of a difference between the time-inverted waveform and the symmetrical waveform, wherein the absorption characteristic calculation circuit repeatedly calculates the waveform of the difference while the time delay applied in the delaying unit is changed, and outputs, as the information representing the absorption characteristics of the sample, the symmetrical waveform or information obtained from the symmetrical waveform when an absolute value of the waveform of the difference is minimized.

5. The absorption characteristic calculation circuit according to claim 4 further comprising:

a waveform correction unit that produces, using parameters prepared in advance and the waveform of the reference driving signal, a corrected waveform by superimposing a distortion on the waveform of the driving signal to provide the corrected waveform closer to a waveform of the laser light output from the quantum cascade laser.

6. An analysis method comprising:

a light generation step of supplying a driving signal including a cyclic waveform to a quantum cascade laser, and converting the driving signal to laser light in a mid-infrared range;

a light detection step of producing a detected signal depending on intensity of the laser light that has passed through a sample; and a data calculation step of producing, on basis of the detected signal, information representing absorption characteristics of the sample, the data calculation step including:

a delaying step of applying, to one of a waveform of a reference driving signal and a waveform of the detected signal, a time delay in comparison with the other waveform;

an adding step of producing a symmetrical waveform by adding the one time-delayed waveform and the other waveform;

a time inversion step of producing a time-inverted signal by inverting a time dependency of the symmetrical waveform; and a subtracting step of producing a waveform of a difference between the time-inverted waveform and the symmetrical waveform, wherein, in the data calculation step, the waveform of the difference is repeatedly calculated while the time delay applied in the delaying step is changed, and the symmetrical waveform or information obtained from the symmetrical waveform when an absolute value of the waveform of the difference is minimized is given as the information representing the absorption characteristics of the sample.

7. The analysis method according to claim 6 further comprising:

a waveform correction step of producing, by using parameters prepared in advance and the waveform of the reference driving signal, a corrected waveform by superimposing a distortion on the waveform of the driving signal to provide the corrected waveform closer to a waveform of the laser light output from the quantum cascade laser.

* * * * *